US009513277B2

(12) United States Patent
Afzali-Ardakani et al.

(10) Patent No.: US 9,513,277 B2
(45) Date of Patent: Dec. 6, 2016

(54) DNA SEQUENCING USING MULTIPLE METAL LAYER STRUCTURE WITH DIFFERENT ORGANIC COATINGS FORMING DIFFERENT TRANSIENT BONDINGS TO DNA

(71) Applicant: International Business Machines Corporation, Armonk, NY (US)

(72) Inventors: Ali Afzali-Ardakani, Ossining, NY (US); Stefan Harrer, Hampton (AU); Binquan Luan, Pleasantville, NY (US); Hongbo Peng, Chappaqua, NY (US); Stephen M. Rossnagel, Pleasantville, NY (US); Ajay K. Royyuru, Congers, NY (US); Gustavo A. Stolovitzky, Riverdale, NY (US); Philip S. Waggoner, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/005,174

(22) Filed: Jan. 25, 2016

(65) Prior Publication Data
US 2016/0139105 A1 May 19, 2016

Related U.S. Application Data

(62) Division of application No. 14/624,868, filed on Feb. 18, 2015, now Pat. No. 9,285,339, which is a division
(Continued)

(51) Int. Cl.
*G01N 33/487* (2006.01)
*B82Y 15/00* (2011.01)
(Continued)

(52) U.S. Cl.
CPC ......... *G01N 33/48721* (2013.01); *B82Y 15/00* (2013.01); *C12Q 1/6869* (2013.01);
(Continued)

(58) Field of Classification Search
CPC .................... G01N 27/3278; G01N 27/44791; G01N 33/48721; C12Q 2565/631; C12Q 1/6869; C12Q 2563/157; B87Y 15/00; Y10S 977/924
See application file for complete search history.

(56) References Cited

U.S. PATENT DOCUMENTS 4,576,829 A  3/1986 Kaganowicz et al.
4,692,992 A  9/1987 Hsu
(Continued)

FOREIGN PATENT DOCUMENTS

CN  101203740 A  6/2008
CN  101385126 A  3/2009
(Continued)

OTHER PUBLICATIONS

S. Chang et al., "Electronic signatures of all four DNA nucleosides in a tunneling gap," Nano Letters, vol. 10, No. 3, 2010, pp. 1070-1075.
(Continued)

*Primary Examiner* — Gurpreet Kaur
(74) *Attorney, Agent, or Firm* — Cantor Colburn LLP; Vazken Alexanian

(57) ABSTRACT

A nanodevice includes a reservoir filled with conductive fluid and a membrane separating the reservoir. A nanopore is formed through the membrane having electrode layers separated by insulating layers. A certain electrode layer has a first type of organic coating and a pair of electrode layers has a second type. The first type of organic coating forms a motion control transient bond to a molecule in the nanopore
(Continued)

for motion control, and the second type forms first and second transient bonds to different bonding sites of a base of the molecule. When a voltage is applied to the pair of electrode layers a tunneling current is generated by the base in the nanopore, and the tunneling current travels via the first and second transient bonds formed to be measured as a current signature for distinguishing the base. The motion control transient bond is stronger than first and second transient bonds.

8 Claims, 8 Drawing Sheets

Related U.S. Application Data of application No. 13/359,766, filed on Jan. 27, 2012, now Pat. No. 8,986,524.

(60) Provisional application No. 61/437,115, filed on Jan. 28, 2011.

(51) Int. Cl.
C12Q 1/68 (2006.01)
G01N 27/447 (2006.01)

(52) U.S. Cl.
CPC . G01N 27/44743 (2013.01); G01N 27/44791 (2013.01); Y10S 977/924 (2013.01)

(56) References Cited

U.S. PATENT DOCUMENTS

| | | | |
|---|---|---|---|
| 5,671,086 A | 9/1997 | Parvin et al. | |
| 6,180,490 B1 | 1/2001 | Vassiliev et al. | |
| 6,217,872 B1 | 4/2001 | Okayama et al. | |
| 6,413,792 B1 | 7/2002 | Sauer et al. | |
| 6,582,926 B1 | 6/2003 | Chilkoti | |
| 6,621,191 B1 | 9/2003 | Nomura et al. | |
| 6,627,067 B1 | 9/2003 | Branton et al. | |
| 6,727,174 B1 | 4/2004 | Kotecki et al. | |
| 6,777,260 B1 | 8/2004 | Chen | |
| 6,783,643 B2 | 8/2004 | Golovchenko et al. | |
| 6,962,849 B1 | 11/2005 | Kamal et al. | |
| 7,282,130 B2 | 10/2007 | Flory | |
| 7,347,921 B2 | 3/2008 | Barth et al. | |
| 7,351,648 B2 | 4/2008 | Furukawa et al. | |
| 7,410,564 B2 | 8/2008 | Flory | |
| 7,468,271 B2 | 12/2008 | Golovchenko et al. | |
| 7,540,717 B2 | 6/2009 | Sheng et al. | |
| 7,553,730 B2 | 6/2009 | Barth et al. | |
| 7,560,141 B1 | 7/2009 | Kim et al. | |
| 7,582,490 B2 | 9/2009 | Golovchenko et al. | |
| 7,846,738 B2 | 12/2010 | Golovchenko et al. | |
| 8,354,336 B2 | 1/2013 | Afzali-Ardakani et al. | |
| 8,852,407 B2 | 10/2014 | Peng et al. | |
| 8,986,524 B2 | 3/2015 | Afzali-Ardakani et al. | |
| 9,121,843 B2 | 9/2015 | Meller et al. | |
| 2004/0180369 A1 | 9/2004 | Franzen et al. | |
| 2005/0019784 A1 | 1/2005 | Su et al. | |
| 2005/0026238 A1 | 2/2005 | Berndt | |
| 2005/0101100 A1 | 5/2005 | Kretchmer et al. | |
| 2005/0102721 A1 | 5/2005 | Barth | |
| 2005/0110990 A1 | 5/2005 | Koo et al. | |
| 2005/0158763 A1 | 7/2005 | Ivanisevic et al. | |
| 2005/0202446 A1 | 9/2005 | Yang et al. | |
| 2006/0105553 A1 | 5/2006 | Wellhausen et al. | |
| 2006/0154399 A1 | 7/2006 | Sauer et al. | |
| 2006/0154400 A1 | 7/2006 | Choi et al. | |
| 2006/0169588 A1 | 8/2006 | Jacobson et al. | |
| 2006/0180469 A1 | 8/2006 | Han et al. | |
| 2006/0246497 A1 | 11/2006 | Huang et al. | |
| 2006/0275778 A1 | 12/2006 | Wu et al. | |
| 2007/0020146 A1 | 1/2007 | Young et al. | |
| 2007/0042366 A1 | 2/2007 | Ling | |
| 2007/0048745 A1 | 3/2007 | Joyce et al. | |
| 2007/0138132 A1 | 6/2007 | Barth | |
| 2007/0187694 A1 | 8/2007 | Pfeiffer | |
| 2007/0190542 A1 | 8/2007 | Ling et al. | |
| 2008/0003571 A1 | 1/2008 | McKernan et al. | |
| 2008/0032290 A1 | 2/2008 | Young | |
| 2008/0102504 A1 | 5/2008 | Akeson et al. | |
| 2008/0105539 A1 | 5/2008 | Lyding et al. | |
| 2008/0119366 A1 | 5/2008 | Sauer et al. | |
| 2008/0187915 A1 | 8/2008 | Polonsky et al. | |
| 2008/0257859 A1 | 10/2008 | Golovchenko et al. | |
| 2009/0136958 A1 | 5/2009 | Gershow et al. | |
| 2009/0188794 A1 | 7/2009 | Simon et al. | |
| 2009/0221443 A1 | 9/2009 | Heller et al. | |
| 2009/0222216 A1 | 9/2009 | Hibbs et al. | |
| 2009/0232724 A1 | 9/2009 | Afzali-Ardakani et al. | |
| 2009/0295372 A1 | 12/2009 | Krstic et al. | |
| 2010/0009134 A1 | 1/2010 | Drndic et al. | |
| 2010/0025249 A1 | 2/2010 | Polonsky et al. | |
| 2010/0025263 A1 | 2/2010 | White et al. | |
| 2010/0032302 A1 | 2/2010 | Holtermann et al. | |
| 2010/0084276 A1 | 4/2010 | Lindsay | |
| 2010/0142259 A1 | 6/2010 | Drndic et al. | |
| 2010/0144535 A1 | 6/2010 | Strachan et al. | |
| 2010/0219339 A1 | 9/2010 | Ogawa et al. | |
| 2010/0252434 A1 | 10/2010 | Roy | |
| 2010/0327255 A1 | 12/2010 | Peng et al. | |
| 2010/0327847 A1 | 12/2010 | Leiber et al. | |
| 2010/0331194 A1 | 12/2010 | Turner et al. | |
| 2011/0052813 A1 | 3/2011 | Ho et al. | |
| 2011/0085759 A1 | 4/2011 | Lee et al. | |
| 2011/0120868 A1 | 5/2011 | Lindsay et al. | |
| 2011/0220574 A1 | 9/2011 | Bakajin et al. | |
| 2011/0236984 A1* | 9/2011 | Sun .................. | C12Q 1/6869 436/94 |
| 2011/0268647 A1 | 11/2011 | Ivanovici et al. | |
| 2011/0279125 A1 | 11/2011 | Bedell et al. | |
| 2012/0076710 A1 | 3/2012 | Waller et al. | |
| 2012/0100627 A1 | 4/2012 | Bekki et al. | |
| 2012/0146162 A1 | 6/2012 | Cho et al. | |
| 2012/0193231 A1 | 8/2012 | Afzali-Ardakani et al. | |
| 2012/0193235 A1 | 8/2012 | Afzali-Ardakani et al. | |
| 2012/0193236 A1 | 8/2012 | Peng et al. | |
| 2012/0193237 A1 | 8/2012 | Afzali-Ardakani et al. | |
| 2012/0288948 A1 | 11/2012 | Lindsay et al. | |
| 2012/0325664 A1 | 12/2012 | Shim et al. | |
| 2013/0037410 A1 | 2/2013 | Xu et al. | |
| 2013/0082233 A1 | 4/2013 | Afzali-Ardakani et al. | |
| 2013/0203050 A1 | 8/2013 | Huber et al. | |
| 2013/0265031 A1 | 10/2013 | Shim et al. | |

FOREIGN PATENT DOCUMENTS

| | | |
|---|---|---|
| EP | 0261592 A1 | 9/1987 |
| EP | 1441213 A1 | 7/2004 |
| EP | 1486775 | 12/2004 |
| WO | 0181908 A | 11/2001 |
| WO | 2006122317 A2 | 11/2006 |
| WO | 2007084163 A | 7/2007 |
| WO | 2008051308 A2 | 5/2008 |
| WO | 2008132643 A1 | 11/2008 |
| WO | 2009020682 A2 | 2/2009 |
| WO | 2009032756 A2 | 3/2009 |
| WO | 2009117522 A2 | 9/2009 |
| WO | 2010107088 A1 | 9/2010 |

OTHER PUBLICATIONS

S. Chang et al., "Chemical recognition and binding kinetics in a functionalized tunnel junction," Nanotechnology, vol. 23, No. 23, 2012, 235101, 14 pages.
S. Harrer et al. "Electrochemical Characterization of Thin Film Electrodes Towards Developing a DNA-Transistor," Langmuir, vol. 26 (24), pp. 19191-19198 (2010).
S. Harrer et al., "Electrochemical Protection of Thin Film Electrodes in Solid State Nanopore," Nanotechnology, vol. 22, 2011, 275304, 6 pages.

(56) References Cited

OTHER PUBLICATIONS

S. Roy et al., "Direct Electrical Measurements on Single-Molecule Genomic DNA Using Single-Walled Carbon Nanotubes," Nano Letters, vol. 8, No. 1, 2008, pp. 26-30.
S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-I.
Schedin F et al: "Detection of Individual Gas Molecules Absorbed on Graphene" Nature Materials Nature Publishing Group, UK, vol. 6, No. 9, Sep. 2007, pp. 652-655, XP002506772, ISSN: 1476-1122, the whole document.
Soni, Gautam V. et al., "Progress toward Ultrafast DNA Sequencing Using Solid-State Nanopores", Clinical Chemistry, vol. 53, No. 11, (2007), pp. 1-6.
Stern, E., et al., "Label-free immunodetection with CMOS-compatible semiconducting nanowires," Nature Letters, vol. 455 Feb. 1, 2007; 2007 Nature Publishing Group; pp. 519-522.
T. D. Harris et al., "Single-molecule DNA Sequencing of a Viral Genome," Science, vol. 320, pp. 106-109 (2008).
T. Kiefer et al., "A single nanotrench in a palladium microwire for hydrogen detection," Nanotechnology, vol. 19, No. 12, 2008, 125502, 9 pages.
T. Nagase et al., "Maskless fabrication of nanogap electrodes by using Ga-focused ion beam etching." Journal of Micro/Nanolithography, MEMS, and MOEMS, vol. 5, No. 1, 2006, 011006, 6 pages.
T. Solomons, et al., "Organic Chemistry," 8th ed., pub. John Wiley & Sons, Inc. Hoboken, NJ 2004; 5 pages.
A. Bergvall et al., "Graphene nanogap for gate-tunable quantum-coherent single-molecule electronics," Phys. Rev. B, vol. 84, No. 15, 2011, 155451, 7 pages.
A. J. Storm et al., "Fabrication of solid-state nanopores with single-nanometre precision," Nature Materials, vol. 2, Aug. 2003, pp. 537-540.
A. K. Geim and K. S. Novoselov, "The Rise of Graphene," Nature Materials 6, 183 (2007), 9 pages.
A. P. Ivanov et al., "DNA tunneling detector embedded in a nanopore," Nano Letters, vol. 11, No. 1, Jan. 12, 2011, pp. 279-285.
A. Sidorenko et al., "Controlled Switching of the Wetting Behavior of Bioimetic Surfaces with Hydrogel-Supported Nanostructures," J. Mater. Chem., vol. 18, 2008, pp. 3841-3846.
A. Yamaguchi, et al., "Self-Assembly of a Silica-Surfactant Nanocomposite in a Porous Alumina Membrane," Nature Materials; vol. 3; May 2004; www.nature.com/naturematerials; pp. 337-341.
Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.
Amit Meller et al., "Rapid nanopore discrimination between single polynucleotide molecules," PNAS, Feb. 1, 2000, vol. 97, No. 3, pp. 1079-1084.
B. Luan et al., "DNA-translocation through a solid state nanopore coated with a self-assembled monolayer," Bull. Am. Phys. Soc., APS March Meeting 2011, vol. 56, No. 1, Abstract V43.00002, Mar. 24, 2011, 1 page.
B. Luan et al., "Tribological Effects on DNA Translocation in a Nanochannel Coated with a Self-Assembled Monolayer," J. Phys. Chem. B, vol. 114, 2010, pp. 17172-17176.
B. Luan, A. Aksimentiev, "Control and Reversal of The Electrophoretic Force on DNA in a Charged Nanopore," J. Phys. Condens. Matter, vol. 22, pp. 454123 (2010).
B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).
Bae, S. et al., "Roll-to-Roll Production of 30-inch Graphene Films for Transparent Electrodes," Nature Nanotechnology, Published online: Jun. 20, 2010, 5 pages.

D. Branton et al., "The Potential and Challenges of Nanopore Sequencing," Nat. Biotech., vol. 26 (10), pp. 1146-1153 Author Manuscript (Oct. 2008); 17 pages.
D. W. Hess, "Plasma-assisted oxidation, anodization, and nitridation of silicon," IBM J. Res. Develop. vol. 43. No. 1/2, Jan./Mar. 1999, pp. 127-145.
Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.
Dubey et al.,"Structure and Order of Phosphonic Acid-Based Self-Assembled Monolayers on Si(100)," Langmuir, vol. 26, No. 18, Sep. 21, 2010, pp. 1-24.
F. Patolsky, et al., "Electrical detection of single viruses,"PNAS; Sep. 28, 2004; vol. 101, No. 39; pp. 14017-14022.
F. S. Collins, M. Morgan, A. Patrinos, "The Human Genome Project—Lessons From Large-scale Biology," Science, vol. 300, pp. 286-290 (2003).
F. Sanger, S. Nicklen, A. R. Coulson, "DNA sequencing with chain termination inhibitors," Proc. Natl. Acad. Sci USA., vol. 74 (12), pp. 5463-5467 (1977).
Free University of Berlin;"Derivatization of Carboxylic Acid With Diazomethane and Trimethylsislydiazomethane: Convenient Methods and Artifacts"; Retrieved from https://web.archive.org/web/2007060100000*/http://userpage.chemie.fu-berlin.de/~tlehmann/krebs/files_diazoalkanes.pdf on Jul. 2, 2015; pp. 1-31.
G. Sigalov, et al., "Detection of DNA Sequences Using an Alternating Electric Field in a Nanopore Capacitor," Nano Letters 2008, vol. 8, No. 1; pp. 56-63.
G. Solomons, et al.,"Organic Chemistry," John Wiley & sons, Inc., Eight Edition, 2004, pp. 1-5.
G. Tizazu et al., "Photopatterning, Etching, and Derivatization of Self-Assembled Monolayers of Phosphonic Acids on the Native Oxide of Titanium," Langmuir, vol. 25, 2009, pp. 10746-10753.
G. Turcatti, A. Romieu, M. Fedurco, A. P. Tairi, "A New Class of Cleavable Fluorescent Nucleotides: Synthesis and Optimization as Reversible Terminators for DNA Sequencing by Synthesis," Nucleic Acids Res., vol. 36, pp. e25 (2008).
G. Wang et al., "Photon Gated Transport at the Glass Nanopore Electrode," J. Am. Chem. Soc., vol. 128, 2006, pp. 13553-13558.
Gracheva, Maria E. et al., "Simulation of the electric response of DNA translocation through a semiconductor nanopore-capacitor", Institute of Physics Publishing, Nanotechnology, vol. 17 (2006), pp. 622-633.
H. Stranneheim, et al., "Stepping Stones in DNA Sequencing," Biotechnical Journal (2012) 7 (9) pp. 1063-1073.
H. W. C. Postma, "Rapid Sequencing of Individual DNA Molecules in Graphene Nanogaps," Nano Letters, vol. 10, No. 2, Jan. 4, 2010, pp. 420-425.
He, et al., "Identification of DNA Basepairing via Tunnel-Current Decay," Nano Letters 2007; vol. 7, No. 12; pp. 3854-3858.
Heng, Jiunn B. et al., "Sizing DNA Using a Nanometer-Diameter Pore", Biophysical Journal, vol. 87, Oct. 2004, pp. 2905-2911.
I. Braslavsky, B. Hebert, E. Kartalov, S. R. Quake, "Sequence Information Can be Obtained from Single DNA Molecules," Proc. Natl. Acad. Sci. USA, vol. 100, pp. 3960-3964 (2003).
International Search Report—PCT; Notification of Transmittal of the International Search Report and The Written Opinion of the International Searching Authority, or The Declaration; Apr. 5, 2011; International application No. PCT/US1123872; pp. 1-8.
J. Hass, W.A. De Heer and E.H. Conrad, "The Growth and Morphology of Epitaxial Multilayer Graphene," Journal of Physics: Condensed Matter 20, 323202 (2008), 28 pages.
J. Li et al., "Ion-beam sculpting at nanometre length scales," Nature, vol. 412, 2001, pp. 166-169.
J. Prasongkit et al., "Transverse conductance of DNA necleotides in a graphene nanogap from first principles," arXiv:1012.1669v2 [physics.ins-det], [v1] Dec. 8, 2010, [v2] Jan. 14, 2011, Nano Lett., vol. 11, No. 5, 2011, pp. 1941-1945.
J. Shedure et al., "Accurate Multiplex Polony Sequencing of an Evolved Bacterial Genome," Science, vol. 309, pp. 1728-1732 (2005).

(56) References Cited

OTHER PUBLICATIONS

Judy Persall, "The Consise Oxford Dictionary," Oxford univeristy Press, 10th edition, 1999, pp. 1-5.
K. Hu, et al., "Use of Atomic Force Microscopy for the Study of Surface Acid-Base Properties of Carboxylic Acid-Terminated Self-Assembled Monolayers," Langmuir 1997, 13, pp. 5114-5119.
K.S. Kim, Y. Zhao, H. Jang, S. Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).
Kasianowicz, John J., et al., "Characterization of individual polynucleotide molecules using a membrane channel", Proc. Natl. Acad. Sci. USA, vol. 93, Nov. 1996, pp. 13770-13773.
Lagerqvist, Johan et al., "Fast DNA Sequencing via Transverse Electronic Transport", Nano Lett., vol. 6, No. 4, Received Jan. 17, 2006; revised Manuscript Received Mar. 1, 2006, pp. 779-782.
M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).
M. J. Kim et al., "Rapid Fabrication of Uniformly Sized Nanopores and Nanopore Arrays for Parallel DNA Analysis," Adv. Mater. 2006, 18, pp. 3149-3153.
M. Margulies et al., "Genome Sequencing in Mircrofabricated High-density Pico-litre Reactors," Nature, vol. 437, pp. 376-380 (2005).
M. Tsutsui et al., "Identifying single nucleotides by tunnelling current," Nature Nanotechnology, vol. 5, 2010, pp. 286-290.
Meller A., Nivon L., Brandin E., Golovchenko J. and Branton D., "Rapid Nanopore Discrimination Between Signle Polynucleotide Molecules," Proc. Natl Acad. Sci. USA 97 1079-84 (2000).
Novoselov K S et al, "Electric Field Effect in Atomically Thin Carbon Films" Oct. 22, 2004 vol. 306 Science; pp. 366-669.
Polonsky et al., "Nanopore in metal-dielectric sandwich for DNA position control," Applied Physics Letters 91, 153103 (2007), pp. 1-3.

* cited by examiner

DNA SEQUENCING USING MULTIPLE METAL LAYER STRUCTURE WITH DIFFERENT ORGANIC COATINGS FORMING DIFFERENT TRANSIENT BONDINGS TO DNA

DOMESTIC PRIORITY

This application is a divisional of U.S. patent application Ser. No. 14/624,868, filed Feb. 18, 2015, which is a divisional application of U.S. patent application Ser. No. 13/359,766 filed Jan. 27, 2012, which claims the benefit of U.S. Provisional Patent Application 61/437,115 filed on Jan. 28, 2011, the contents of which are herein incorporated by reference in their entirety.

BACKGROUND

Exemplary embodiments relate to nanodevices, and more specifically to a multiple layer structure with one or more organic coatings.

Nanopore sequencing is a method for determining the order in which nucleotides occur on a strand of deoxyribonucleic acid (DNA). A nanopore can be a small hole in the order of several nanometers in internal diameter. The theory behind nanopore sequencing is about what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods. For example, an electric field might attract the DNA towards the nanopore, and it might eventually pass through the nanopore. The scale of the nanopore can have the effect that the DNA may be forced through the hole as a long string, one base at a time, like thread through the eye of a needle.

BRIEF SUMMARY

According to an exemplary embodiment, a nanodevice is provided. The nanodevice includes a reservoir filled with a conductive fluid, and a membrane separating the reservoir, where the membrane includes electrode layers separated by insulating layers. A nanopore is formed through the membrane. A certain electrode layer has a first type of organic coating and a pair of electrode layers has a second type of organic coating inside the nanopore. The first type of organic coating on the certain electrode layer forms a motion control transient bond to a molecule in the nanopore for motion control of the molecule, and the second type of organic coating on the pair of electrode layers forms first and second transient bonds to different bonding sites of a base of the molecule in the nanopore. When a voltage is applied to the pair of electrode layers a tunneling current is generated by the base in the nanopore, and the tunneling current travels via the first and the second transient bonds formed to the base to be measured as a current signature for distinguishing the base. The motion control transient bond is stronger than the first and the second transient bonds.

According to an exemplary embodiment, a system is provided. The system includes a nanodevice. The nanodevice includes a reservoir filled with a conductive fluid, and a membrane separating the reservoir, where the membrane includes electrode layers separated by insulating layers. A nanopore is formed through the membrane. A certain electrode layer has a first type of organic coating and a pair of electrode layers has a second type of organic coating inside the nanopore. The first type of organic coating on the certain electrode layer forms a motion control transient bond to a molecule in the nanopore for motion control of the molecule, and the second type of organic coating on the pair of electrode layers forms first and second transient bonds to different bonding sites of a base of the molecule in the nanopore. The system includes a voltage source configured to apply a voltage. When the voltage is applied by the voltage source to the pair of electrode layers a tunneling current is generated by the base in the nanopore, and the tunneling current travels via the first and the second transient bonds formed to the base to be measured as a current signature for distinguishing the base. The motion control transient bond is stronger than the first and second transient bonds.

According to an exemplary embodiment, a nanodevice is provided. The nanodevice includes a reservoir filled with a conductive fluid, and a membrane separating the reservoir, where the membrane includes electrode layers separated by insulating layers. A nanopore is formed through the membrane. A certain electrode layer has a first type of organic coating and a pair of electrode layers has a second type of organic coating inside the nanopore. The first type of organic coating on the certain electrode layer forms a motion control transient bond to a molecule in the nanopore for motion control of the molecule. The second type of organic coating on the pair of electrode layers forms a first transient bond to a first base and a second transient bond to a second base of the molecule in the nanopore. When a voltage is applied to the pair of electrode layers a tunneling current is generated though the first base along the molecule to the second base in the nanopore. The tunneling current travels via the first and the second transient bonds respectively to be measured as a current signature for distinguishing the first base and the second base. The motion control transient bond is stronger than the first and the second transient bonds.

According to an exemplary embodiment, a nanodevice is provided. The nanodevice includes a substrate, a nanochannel formed in the substrate, a first pair of electrodes having a nanometer size gap there between, and a second pair of electrodes having a nanometer size gap there between. The first and second pair of electrodes are positioned along the nanochannel and in the substrate. A first organic coating is on an exposed surface of the first pair of electrodes at an inner surface of the nanochannel. The first organic coating forms a first transient bond between the first pair of electrodes and a base of a molecule in the nanochannel. A second organic coating is on an exposed surface of the second pair of electrodes at an inner surface of the nanochannel. The second organic coating forms a second transient bond between the second pair of electrodes and another base of the molecule in the nanochannel. When a first voltage is applied to the first pair of electrodes, a tunneling current is generated by the base in the nanochannel. The tunneling current travels through the first transient bond formed to the base to be measured as a current signature for distinguishing the base.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

DETAILED DESCRIPTION

Exemplary embodiments provide an organic-coated nanopore through a stack of repetitive insulating/conducting/insulating/conducting/insulating/ . . . layers. Exemplary embodiments leverage the transient bonding between the organic coating and the DNA bases to control the motion of the DNA, and then utilize the tunneling current through the DNA base for differentiating the DNA base while the DNA base is transiently bonded to the organic coating.

Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/ human genome. Two issues in nanopore DNA sequencing are controlling the translocation of DNA through the nanopore and differencing individual DNA bases.

As illustrated in an exemplary embodiment, the use of a nanopore through a stack of repetitive insulating/conducting/insulating/conducting/insulating/ . . . layers is proposed, and all conductive surfaces at the inner-surface of the nanopore are coated with an organic layer, which can transiently bond to individual DNA bases. Thus, the DNA can be temporarily trapped inside the nanopore when enough of these transient bonds are present. The negatively charged DNA can be controllably driven through the nanopore by an external electrical field along the nanopore if one tunes the electrical field to alternatively be above and below the threshold of breaking all transient bonds. All conducting layers are electrically addressed by respective voltage sources and the tunneling current between adjacent conductive layers is measured while individual DNA bases are temporally bonded to them. Since DNA bases are temporarily fixed during the measurements, the tunneling current will have enough resolution to differentiate DNA bases. Note that multiple conducting layers provide the necessary trapping energy (e.g., multiple bonding locations) of DNA as well as redundant data of tunneling current for error check. DNA can also be driven back and forth through the nanopore many times by switching the polarity of the external electrical field of the voltage source, for repeated measurements.

According to an exemplary embodiment, multiple conducting layers are differentially coated so that some bonds will be optimized for motion control and other bonds will be optimized for DNA base sensing. The multiple conducting layers can also be made from two or more different materials so that different organic coatings can be applied to each material of the conducting layers.

Figure 1:
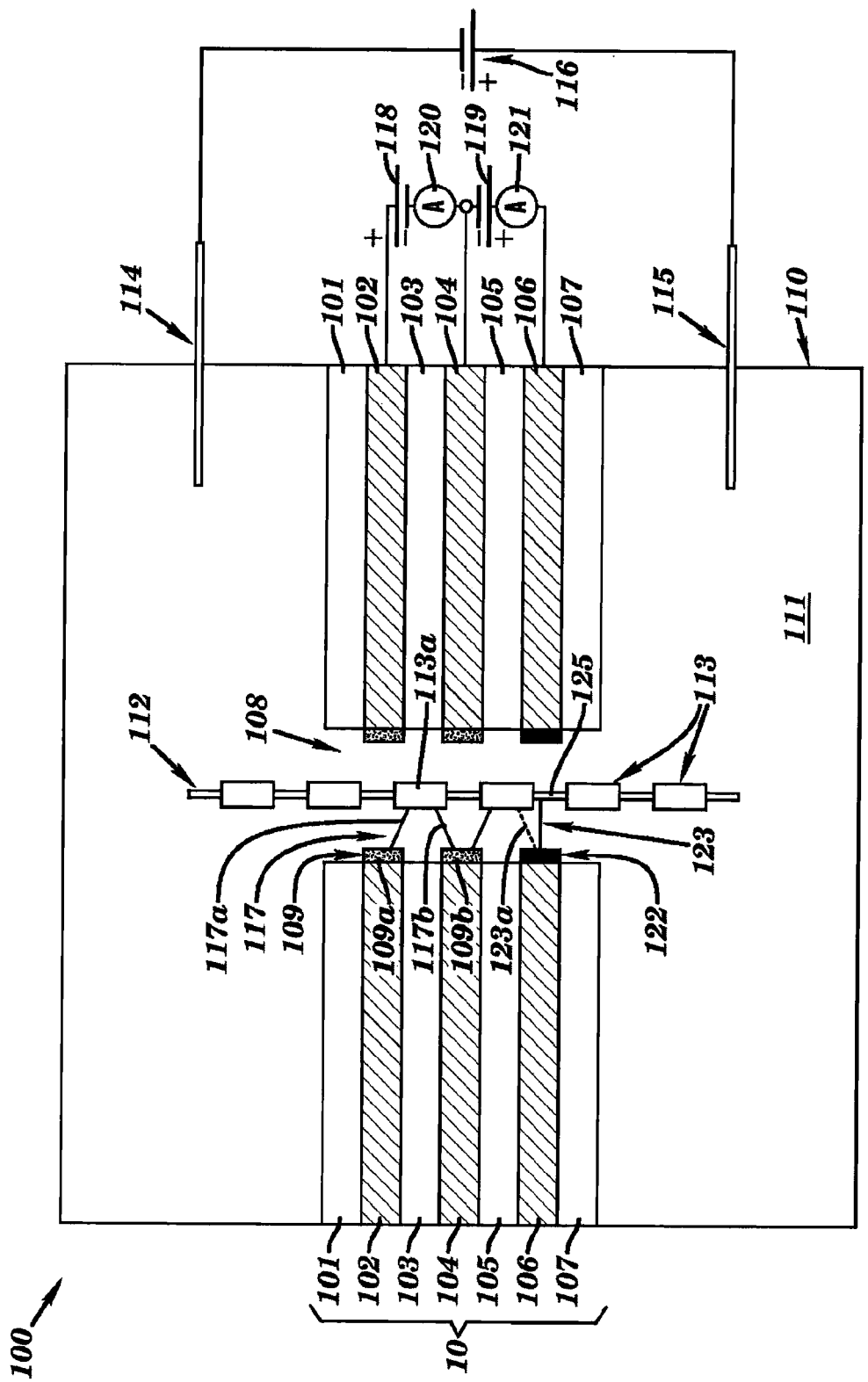
FIG. 1 illustrates a schematic of a nanopore device in accordance with an exemplary embodiment.

Now turning to FIG. 1, FIG. 1 illustrates a schematic 100 of an organic-coated nanopore through a stack of repetitive insulating/conducting/insulating/conducting/insulating/ . . . layers for DNA motion control and base sensing, for the case that tunneling current is measured through a single DNA base according to an exemplary embodiment.

A membrane 10 is made of films 101, 102, 103, 104, 105, 106, and 107, and the membrane 10 partitions a reservoir 110 into two parts. FIG. 1 is a cross-sectional view of the reservoir 110. A nanometer size hole 108 is made through the membrane 10. Membrane part 101, 103, 105, and 107 are electrically insulating while membrane parts 102, 104, and 106 are electrically conducting. Layers 101 and 107 are electrical passivation layers, and layers 103 and 105 are insulating inter-layers between conductive layers. Only three conductive layers 102, 104, and 106 are shown in the FIG. 1, but exemplary embodiments are not limited to three conductive layers. It is contemplated that two or more conductive layers may be utilized. The conductive layers 102, 104, and 106 are electrodes and may also be referred to as electrodes herein.

Organic coating 109 is made on the surface of conductive layers 102 and 104, while organic coating 122 is made on the surface of conductive layer 106. Organic coating 109 and 122 can be any organic coating that has transient bonding 117 and 123 respectively (such as, e.g., a hydrogen bond) with individual DNA bases 113 and/or DNA backbone 125 (for organic coating 122). The DNA backbone 125 is the line between (i.e., connecting) DNA bases 113. The minimum number of conductive layers is determined by the need for trapping DNA molecules 112 (i.e., DNA) inside the nanopore against thermal agitation via the transient bonds 117 and 123. The reservoir 110 and the nanopore 108 are then filled with solvent 111 (e.g., a conducive solution). DNA molecules 112 (in which bases are illustrated as 113 and the backbone is illustrated as 125) are loaded into the nanopore 108 by an electrical voltage bias of voltage source 116 (which produces an electric field), applied across the nanopore 108 via two electrochemical electrodes 114 and 115, which were dipped in the solvent 111 of the two parts of reservoir 110.

With the desired number of conductive layers 102, 104, and 106 (thus producing enough transient bonds 117 and 123), the DNA molecule 112 can be trapped inside the nanopore 108 against thermal motion. With a predefined voltage of the voltage source 116, these transient bonds 117 and 123 can be broken, and the DNA 112 can be driven through the nanopore 108 via the electrical field produced by the voltage source 116. If the voltage source 116 is pulsed, the DNA 112 will (alternately) experience a bonded phase (fixed in position) and moving phase. At the bonded phase, voltages of voltage sources 118 and 119 can be applied between adjacent conductive layers 102 and 104, and/or adjacent conductive layers 104 and 106 respectively. Accordingly, tunneling current 120 can be measured by its corresponding ammeter (A), and tunneling current 121 can be measured by its corresponding ammeter (A). Since the DNA base 113 is fixed during the bonding phase, these tunneling current (signatures) 120 and 121 can be used to identify individual DNA bases 113. The moving phase (when the voltage source 116 is applied) will advance the DNA 112 through the nanopore 108 for identifying other DNA bases 113. The DNA 112 can also be driven back and forth through the nanopore 108 many times by switching the polarity of the external voltage bias of voltage source 116, for repeated measurements.

Note that organic coating 109 (corresponding to organic coating 209 in FIG. 2) and organic coating 122 (corresponding to organic coating 222 in FIG. 2) are different. For example, organic coating 109 is optimized for base sensing (via tunneling current) while organic coating 122 is optimized for motion control (i.e., preventing thermal motion of the DNA 112 in the nanopore 108). In some exemplary embodiments, the organic coating 109 consists of bifunctional small molecules which at one end (first functionality) form covalent bonds with electrodes (e.g., conductive layers 102 and 104). At the other end (second functionality) of the organic coating 109 which is exposed in the nanopore 108, the organic coating 109 consists of functionalities which can form hydrogen bonds with DNA and/or can protonate nucleotides to form acid base interactions.

If the (electrodes) conductive layers 102 and 104 are made of metals such as gold, palladium, platinum etc., the first functionality which bonds to conductive layers 102 and 104 can be chosen as thiols, isocyanides, and/or diazonium salts. If the conductive layers 102 and 104 are made of titanium nitrides or indium tin oxide (ITO), the covalent bonding functionality is chosen from phosphonic acid, hydroxamic acid, and/or resorcinol functionality. The small bifunctional molecules are designed in such a way that any charge formation due to interaction with DNA can easily be transferred to the conductive layers 102 and 104 and therefore a pi-conjugated moiety (e.g. benzene, diphenyl, etc.) are sandwiched between two functionalities. The second functionality is a group which can form a strong hydrogen bond with DNA. Examples of such groups include but are not limited to alcohols, carboxylic acids, carboxamides, sulfonamides, and/or sulfonic acids.

The organic coating 122 which is designed for motion control, can be the same as organic coating 109 listed above, but is made on conductive layer 106 which is much thicker (e.g., two, three, four, five . . . nine, etc., times thicker) than conductive layers 102 and 104, and this greater thickness of the conductive layer 106 causes organic coating 122 to form more transient bonds with DNA 112 (than organic coating 109 on conductive layers 102 and 104). Further, the organic coating 122 could also be derivatized individual nucleic base which can self-assemble on titanium nitride (TiN) electrodes (such as conductive layer 106). Derivatized individual nucleic bases can form multiple hydrogen bonds with DNA 112, thus providing stronger transient bonding.

Figure 5:
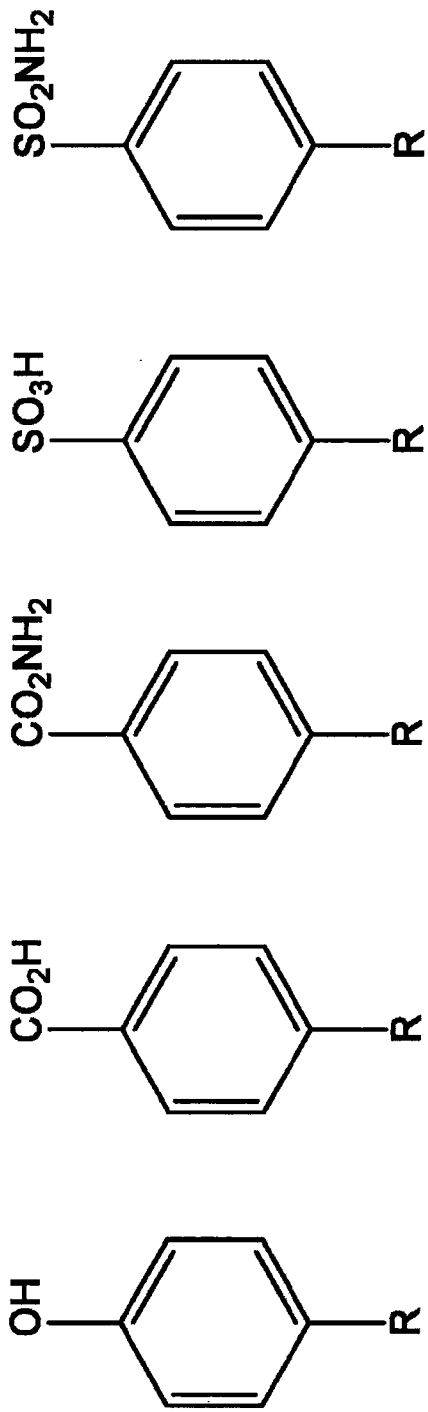
FIG. 5 illustrates molecules of the organic coating according to an exemplary embodiment.

FIG. 5 illustrates examples of molecules for the organic coating 109 (including organic coating 209) and/or for the organic coating 122 (including organic coating 222) according to an exemplary embodiment. In FIG. 5, the example molecules are for self-assembly inside nanopore 108 and/or 208 in FIG. 2. As discussed herein, note that the examples for the organic coating 109 apply to the organic coating 209, and the examples for the organic coating 122 apply to the organic coating 222.

The organic coating 109 on conductive layers 102 and 104 are designed to form transient bonds 117 to the DNA bases 113 of the DNA molecule 112 (and are not able/designed to form transient bonds to the DNA backbone 125). The transient bond 117 formed by the organic coating 109 is weaker than the transient bond 123 formed by the organic coating 122. For example, the transient bond 123 is stronger than the transient bond 117 in the sense that the transient bond 123 is able to hold the DNA molecule 112 in place (i.e., in a fixed position) against thermal motion (thermal agitation) of the DNA molecule 112 in the nanopore 108. Thermal motion causes the DNA molecule 112 to move inside the nanopore 108 even when no voltage is applied by the voltage source 116. The thermal motion is great enough to break the transient bonds 117 formed by the organic coating 109 on the conductive layers 102 and 104 but is not great enough (i.e., not strong enough) to break the transient bond 123 formed by organic coating 122 on the conductive layer 106. As such, the transient bond 123 between the conductive layer 106 (via organic coating 122) and the backbone 125 controls the motion of the DNA molecule 112 inside the nanopore 108. During the moving phase, the voltage is applied by the voltage source 116 to move (i.e., to break the transient bonds 123 and 117) the DNA molecule 112 in the nanopore 108.

Although the transient bond 123 is shown as being connected (bonded) to the backbone 125, the transient bond 123 produced by the organic coating 122 can also bond to the DNA base 113 (via the transient bond 123a illustrated with dotted line). Also, although not shown for conciseness, the organic coating 122 can be applied to multiple conductive layers (e.g., 2, 3, 4, 5, etc.), and the total transient bonding strength of the conductive layers with organic coatings 122 is the sum of their respective transient bonds 123. In some embodiments that are not shown in the figure for conciseness, organic coating 122 can also be made/applied on the surface of the insulating layers 101, 103, 105, 107 that are inside of the nanopore 108, to enhance the trapping of DNA 112 inside the nanopore 108.

In the following example, when the DNA 112 is driven into the nanopore 108 by the voltage source 116, a DNA base 113a forms a transient bond 117 via the organic coating 109 with the (electrode) conductive layer 102 and the conductive layer 104. The organic coating 109 applied on the ends of the conductive layers 102 and 104 forms a chemical bond (i.e., transient bond 117) with base 113a. For explanation purposes and to ease understanding, the transient bonds 117a and 117b connecting the base 113a to conductive layers 102 and 104 (respectively) may be viewed as wires connecting the base 113a to the conductive layers 102 and 104. When the voltage source 118 is turned on (during the bonded phase), current flows through conductive layer 102, then through organic coating 109a, through the transient bond 117a, into the base 113a (which causes the tunneling current 120), out through the transient bond 117b, into the organic coating 109b, into conductive layer 104, and into the ammeter A designated for measuring the tunneling current 120 of the base 113a. When the tunneling current 120 is being measured as discussed above, the organic coating 122 on the (electrode) conductive layer 106 forms the strong transient bond 123 (i.e., chemical bond) to the backbone 125 and/or the base 113 (by the dotted line for transient bond 123a), in which the transient bond 123 holds the DNA molecule 112 in a fixed position against thermal motion that would normally move the DNA molecule 112 in the nanopore 108. For example, if the transient bond 123 were absent, the thermal motion would move the DNA 112 in the nanopore, such that this movement would break the transient bonds 117a and 117b and prevent the ammeter from measuring the tunneling current 120 of the DNA base 113a.

The measured tunneling current 120 is a unique current signature of the base 113a which is utilized to identify (characterize) the base 113a (by a software application 605 of a computer 600), as well as subsequent bases 113 having their respective tunneling currents measured. Note that, the tunneling current 120 between conductive layers 102 and 104 does not require any electrical wiring between them as the electrons simply move from one electrode/conductive layer to the other in a quantum mechanical way. There will be a baseline tunneling current when DNA base 113a is away (e.g., with distance much longer than the wavelength of an electron) from the two (electrodes) conductive layers 102 and 104. When DNA base 113a is close (e.g., within the distance of a wavelength of an electron) to the two (electrodes) conductive layers 102 and 104, the tunneling path of the electron will be rerouted to tunnel from one electrode (e.g., conductive layer 102) to the DNA base 113a and then to the other electrode (e.g., conductive layer 104). In this way, the tunneling current (by the electrons) will create a signature (such as an increasing of the baseline tunneling current, typically in the order of tens of pA (picoamperes)) added onto the baseline tunneling current trace. The tunneling current across DNA bases is dependent on the electronic and chemical structure of the DNA bases, thus each different DNA base will generate a different tunneling current signature. The organic coating 122 and 109 form transient bonds 123 and 117 respectively with DNA 112, which will help to fix the orientation of the DNA base and the relative distance of the DNA base to the electrodes/conducive layers for improving the resolution of the tunneling current signatures. If organic coating 109 and/or bonding 107 is electrically conductive, they will help to shrink the tunneling gap size and enhance the tunneling current signatures too. If the difference between the tunneling current signatures of different DNA bases is small or stochastic, repeating measurements on the same DNA base can be done, a histogram of the amplitudes of the tunneling current signatures can be fit, and the statistical data will provide enough resolution to differentiate DNA bases 113.

Although the above example explains how the two conductive layers 102 and 104 are used to measure the tunneling current 120 for base 113a in the nanopore 108, any two layers of conductive layers 102, 104, and 106 can be utilized to measure any of the bases 113. For example, when the base 113a is driven further through the nanopore 108 (or for a different base 113), using voltage source 119 and conductive layers 104 and 106, the tunneling current 121 for the base 113a can be measured again with a corresponding ammeter A. Also, with multiple layers of conductive layers and insulating layers in the membrane 10 and with multiple voltage sources and ammeters, the tunneling current for different bases 113 can be simultaneously measured in the nanopore 108 during the bonded phase as discussed herein.

Figure 2:
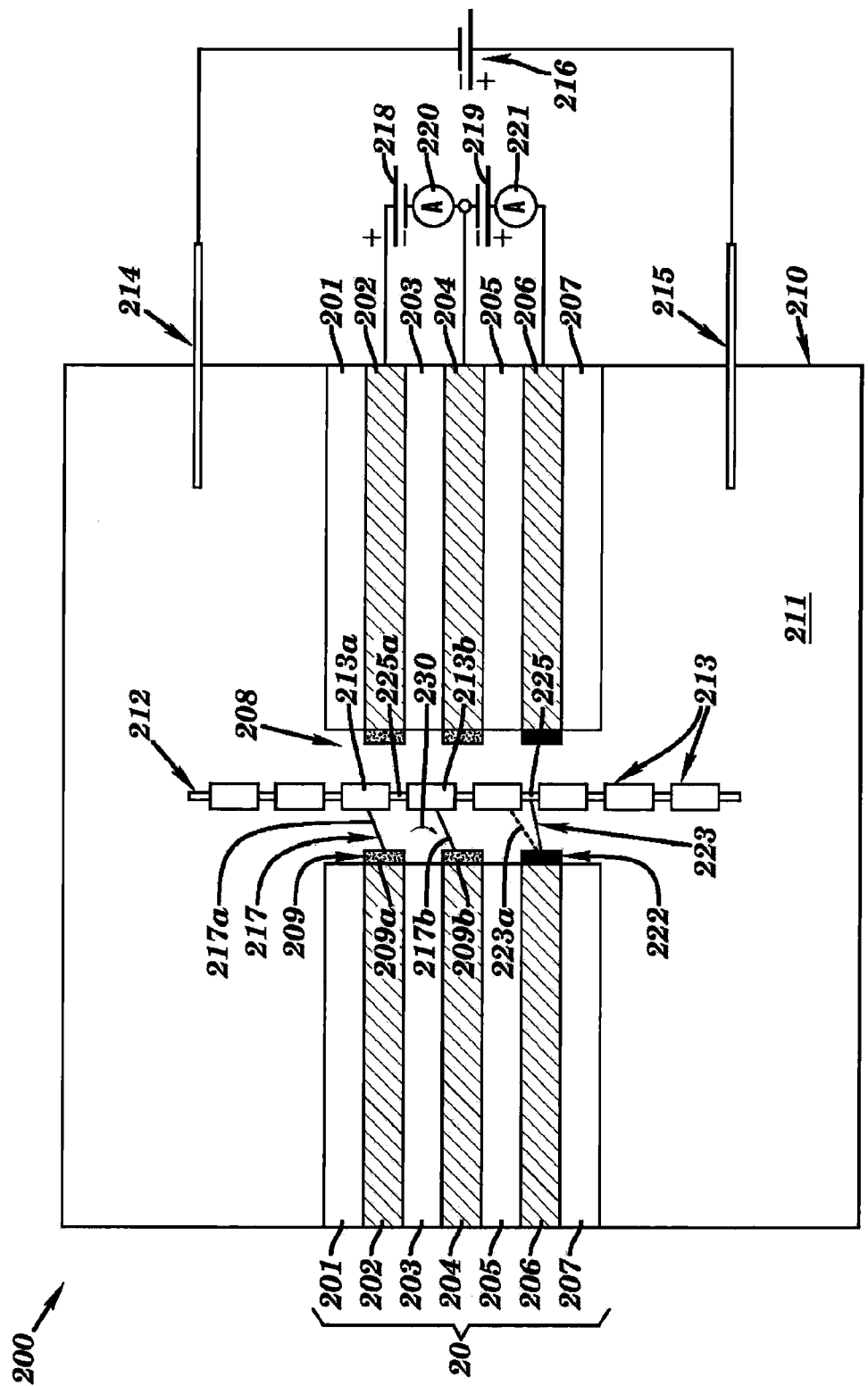
FIG. 2 illustrates a schematic of a nanopore device in accordance with an exemplary embodiment.

Now turning to FIG. 2, FIG. 2 illustrates a schematic 200 of an organic-coated nanopore through a stack of repetitive insulating/conducting/insulating/conducting/insulating/ . . . layers for DNA motion control and base sensing, for the case that tunneling current is measured through a sequence of several DNA bases according to an exemplary embodiment.

In FIG. 2, a membrane 20, which is made of films 201, 202, 203, 204, 205, 206, and 207, partitions a reservoir 210 into two parts. The schematic 200 is a cross-sectional view of the reservoir 210. A nanometer size hole 208 is made through the membrane 20. Membrane parts 201, 203, 205, and 207 are electrically insulating while membrane parts 202, 204, and 206 are electrically conducting. The films 201 and 207 are electrical passivation layers, and the films 203 and 205 are insulating inter-layers between conductive layers. Three conductive layers 202, 204, and 206 are shown in the FIG. 2 but exemplary embodiments are not limited to three conductive layers. It is contemplated that two or more conductive layers may be utilized. The conductive layers 202, 204, and 206 are electrodes and may be considered as electrodes or electrode layers herein. An organic coating 209 (like the organic coating 109 in FIG. 1) is made on the (inner) surface of conductive layers 202 and 204, and an organic coating 222 (like the organic coating 122 in FIG. 1) is made on the (inner) surface of the conductive layer 206.

The example implementation in FIG. 2 is almost identical to FIG. 1, except that the transient bonds 217 from adjacent conductive layers are linked to different DNA bases 213 instead of a single base (like base 113a in FIG. 1) connecting to two conductive layers. Thus, the tunneling currents (signatures) 220 and 221 will be associated with one or more DNA bases 213. This provides a faster DNA sequencing speed but requires more resolution on the tunneling signals (such as tunneling current signature 220) to resolve $4^n$ types of signals (where n is the number of bases 213 along the tunneling path, and where 4 is the total number of different DNA bases). One skilled in the art understands the different types of DNA bases.

Figure 4:
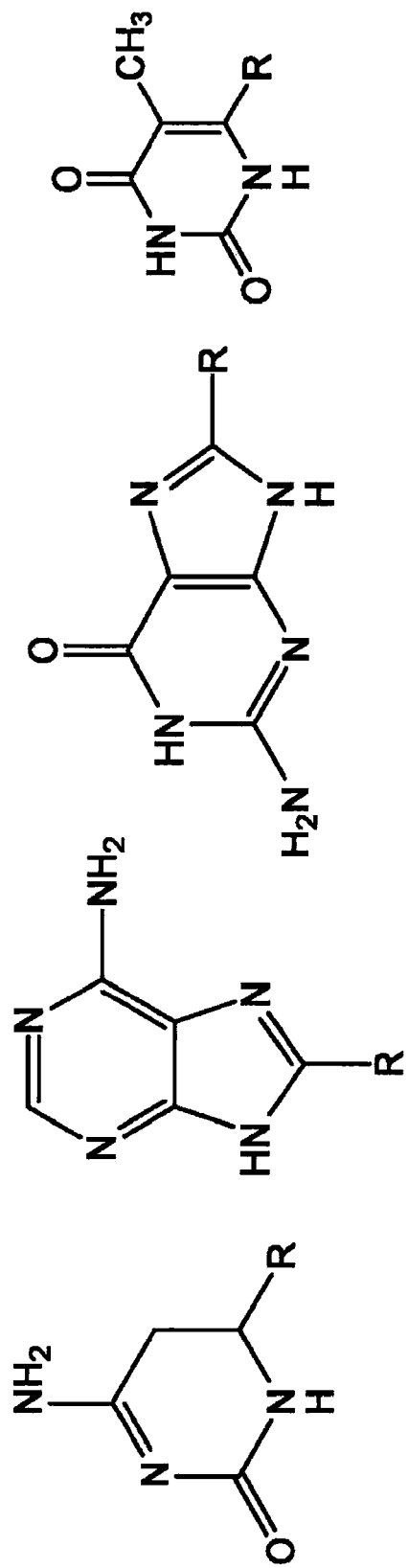
FIG. 4 illustrates molecules of the organic coating according to an exemplary embodiment.

As discussed above for organic coating 109 and 122, note that organic coating 209 and 222 are respectively different. For example, organic coating 209 is optimized for base sensing while organic coating 222 is optimized for motion control (i.e., preventing thermal motion of the DNA 212 in the nanopore 208). FIG. 4 illustrates examples of the molecules for the organic coating 222 according to an exemplary embodiment. In FIG. 4, the example molecules of the organic coating 222 are for self-assembly inside the nanopore 208. FIG. 5 illustrates examples of the molecules for the organic coating 209 and 222 according to an exemplary embodiment. In FIG. 5, the example molecules of the organic coating 209 and/or 222 are for self-assembly inside the nanopore 208.

The organic coating 209 on conductive layers 202 and 204 is designed to form transient bonds 217 to the bases 213 of the DNA molecule 112 (and are not able to form transient bonds to the DNA backbone 225). The transient bonds 217 formed by the organic coating 209 is weaker than the transient bond 223 formed by the organic coating 222. For example, the transient bond 223 is stronger than the transient bond 217 in the sense that the transient bond 223 is able to hold the DNA molecule 212 in place (i.e., in a fixed position) against thermal motion (thermal agitation) of the DNA molecule 212 in the nanopore 208. The thermal motion is great enough to break the transient bonds 217 formed by the organic coating 209 on the conductive layers 202 and 204 but not strong enough to break the transient bonds 223 formed by organic coating 222 on the conductive layer 206. Although the transient bond 223 is shown as being connected (bonded) to the backbone 225, the transient bond 223 produced by the organic coating 222 can also bond to the DNA base 213 (as shown by the transient bond 223a which represented with a dotted line). Also, although not shown for conciseness, the organic coating 222 can be applied to multiple conductive layers (e.g., 2, 3, 4, 5, etc.), and the total transient bonding strength of the multiple conductive layers having organic coatings 222 is the sum of their respective transient bonds 223. In some exemplary embodiments that are not shown for conciseness, the organic coating 222 can also be made on the surface of the insulating layers 201, 203, 205, 207 that are inside of the nanopore 208, to enhance the trapping of DNA 212 inside the nanopore 208.

Figure 6:
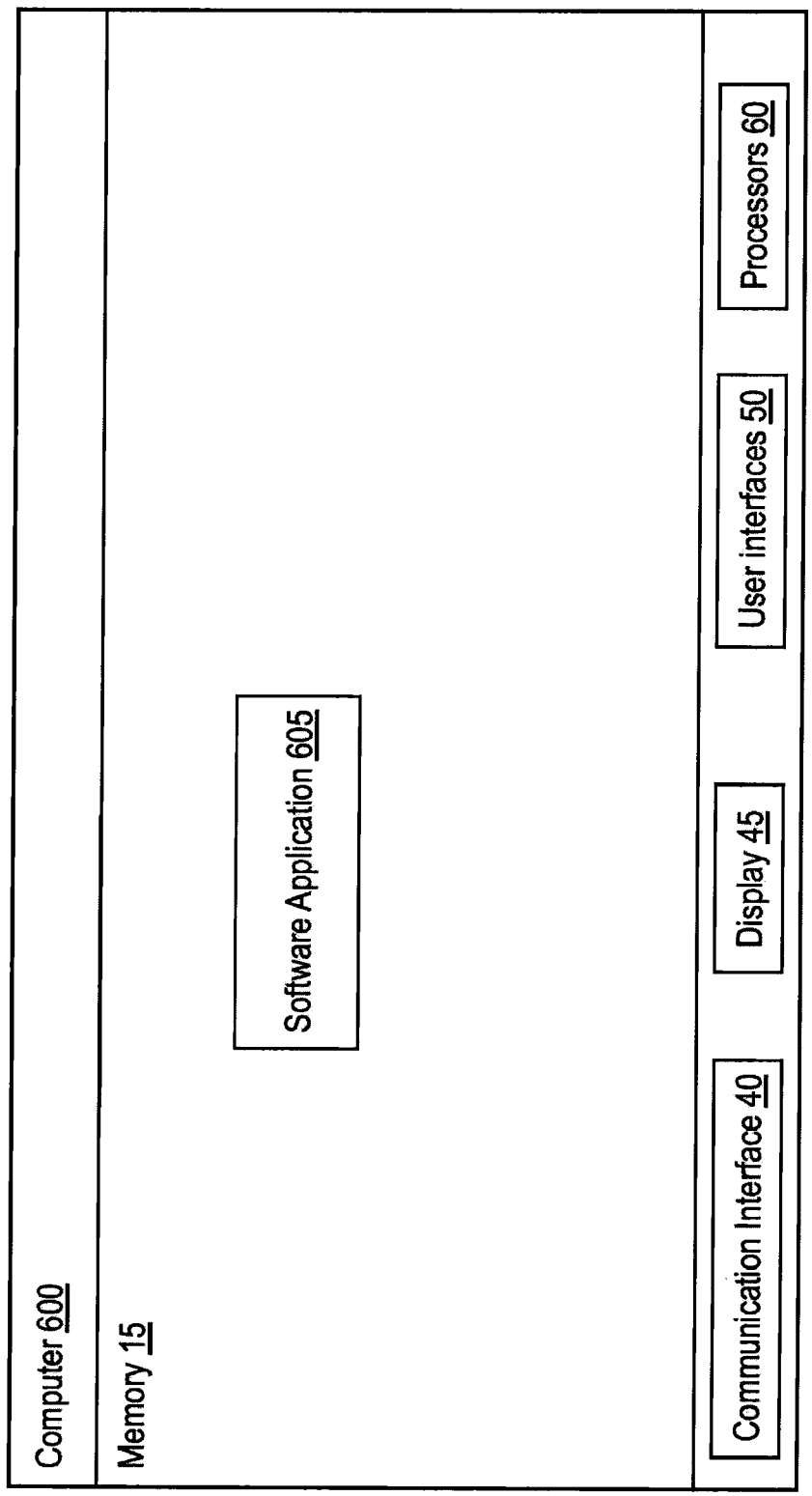
FIG. 6 illustrates a computer utilized according to exemplary embodiments.

An example tunneling path 230 will be discussed when the strong transient bond 223 via organic coating 222 holds the DNA molecule in place against thermal motion. The voltage source 216 produces an electric field to drive the DNA molecule 212 into the nanopore 208. When the voltage source 218 is turned on (during the bonded phase), current flows through the conductive layer 202, through the organic coating 209a, through the transient bond 217a, into the DNA base 213a, through the DNA molecule backbone 225a connecting DNA bases 213a and 213b, into the DNA base 213b, out through the transient bond 217b, out through the organic coating 209b, into the conductive layer 204, and into an ammeter A designated to measure tunneling current 220. In this example, when the ammeter A measures the tunneling current 220, the ammeter actually measures (a combined/composite tunneling current 220 contributed to by both the DNA bases 213a and 213b) the tunneling current through a tunneling path 230 combined of the base 213a and the base 213b. As discussed above, the tunneling current 220 (signal) through the tunneling path 230 combined of the base 213a and the base 213b has to be analyzed in order to identify individual DNA bases 213a and 213b. FIG. 6 illustrates a computer 600 having a software application 605 configured with executable instructions to analyze the tunneling current 220 and thus determine the combination of the base 213a and the base 213b. There are 4 types of DNA bases and a total of 16 types of combinations of the base 213a and the base 213b. Different combinations of the base 213a and the base 213b will generate a different tunneling current 220. If the difference between the tunneling current of different combinations of bases is small or stochastic, repeating measurements on the same combination of DNA bases can be done, a histogram of the amplitudes of the tunneling current signatures can be fit, and the statistical data will provide enough resolution to identify the exact combination of DNA bases. If DNA 212 advances just one base after measuring the tunneling current for the combination of the base 213a and base 213b, the new combination of DNA bases under measurement will have a difference of only one base from the previous measured combination. This will generate redundant/extra data for error checking.

Figure 3:
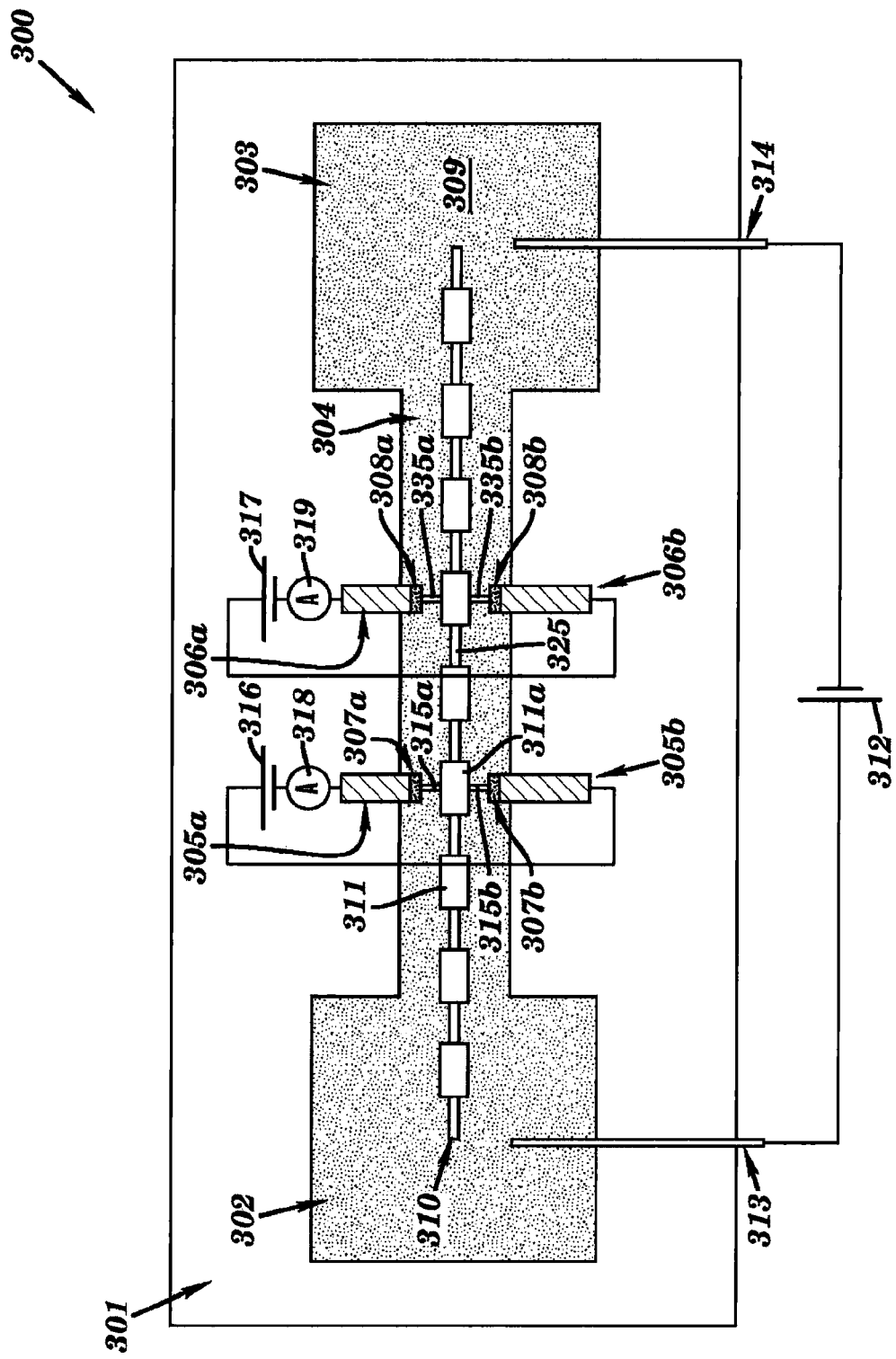
FIG. 3 illustrates a schematic of a nanopore device in accordance with an exemplary embodiment.

Referring to FIG. 3, a schematic 300 is illustrated of an organic-coated nanochannel with multiple tunneling electrodes for DNA motion control and base sensing according to an exemplary embodiment. FIG. 3 illustrates a "lateral nanochannel" version of the implementations discussed for FIGS. 1 and 2. FIG. 3 is a top cross-sectional view of the schematic 300. The nanodevice is FIG. 3 includes a substrate 301 which may be made of any insulating and/or semiconductor solid material.

Two reservoirs 302 and 303 are etched into the substrate 301, and a lateral nanochannel 304 connects the reservoirs 302 and 303. Reservoir 302, reservoir 303, and nanochannel 304 are then filled with ionic solvent 309. Electrodes 305a and 305b (generally referred to as electrodes 305) are a pair of electrodes with a nanometer size gap between them, and the end of each electrode 305a and 305b is integrated within the nanochannel 304 while the other end is in the substrate 301. Electrodes 306a and 306b (generally referred to as electrodes 306) are another pair of electrodes with a nanometer size gap between them, and the end of each electrode 306a and 306b is integrated within the nanochannel 304 while the other end is in the substrate 301. Although only two pairs of electrodes (electrodes 305 and 306) are shown in FIG. 3, it is contemplated that electrodes of one or more pairs (e.g., 3, 4, 5, 6, 7, and/or 10 pairs of electrodes) may be utilized as discussed herein.

Organic coating 307a and 307b (generally referred to as organic coating 307) are made on the exposed surface of electrodes 305a and 305b in the nanochannel 304, and organic coating 308a and 308b (generally referred to as organic coating 308) are made on the exposed surface of electrodes 306a and 306b. The organic coating 307 can be any organic coating that has a transient bond 315, such as a hydrogen bond, with individual DNA bases 311 (DNA 310 illustrates the whole DNA molecule). The organic coating 308 can be any organic coating that has a transient bond 335, such as a hydrogen bond, to individual DNA bases 311 and/or DNA backbones 325 of the whole DNA molecule 310. The minimum number of pairs of electrodes is determined by the need (of the user) for trapping DNA molecules 310 inside the nanochannel 304 (i.e., similar to the nanopores 108 and 208) against thermal agitation via these transient bonds 315 and 335. DNA molecules 310 were loaded into the nanochannel 304 by an electrical voltage bias of voltage source 312 (producing an electric field) applied across the nanochannel 304 via two electrochemical electrodes 313 and 314, which were dipped in the solvent 309 of the two reservoirs 302 and 303.

With enough pairs of electrodes (e.g., two), thus enough transient bonds 315 and/or 335, the DNA molecule 310 can be trapped inside the nanochannel 304 against thermal motion (e.g., when the voltage of voltage source 312 is not applied). With a predefined voltage applied by voltage source 312, these transient bonds 315 and 335 can be broken, and the DNA molecule 310 can be driven through the nanochannel 304 via the electrical field. If the voltage source 312 is pulsed, the DNA molecule 310 will experience a bonded phase and a moving phase (as discussed above). During the bonded phase, voltages sources 316 and 317 can be applied on electrode pair 305 and 306 respectively. Tunneling currents 318 and 319 can be measured with ammeters A respectively corresponding to each tunneling current 318 and 319. Since the DNA base 311 is in a fixed bonded position by the transient bonds 315 and 335, these measured tunneling current (signatures) 318 and 319 can be used to identify individual DNA bases 311 by the software application 605 of the computer 600, e.g., by a user utilizing the computer 600 (to view the tunneling current signatures 318 and 319), and/or by a user viewing the corresponding ammeters A. The moving phase will advance the DNA molecule 310 for identifying other DNA bases 311. The DNA 310 can also be driven back and forth through the nanochannel 304 many times by switching the polarity of the external voltage bias of the voltage source 312, for repeated measurements.

Note that the organic coating 307 and 308 are different. Organic coating 307 (the same as organic coatings 109 and 209) is optimized for base 311 sensing while organic coating 308 (the same as organic coating 122 and 222) is optimized for motion control (i.e., stopping the thermal motion from moving the DNA molecule 310). In one exemplary embodiment, electrode (metal) 305 may be TiN, and electrode 306 may be gold (Au), platinum, and/or silver. The organic coating 307 which is designed for base sensing could be a derivatized individual nucleic base which can self-assemble on TiN electrodes 305. For example, these organic coatings 307 could be formed by individual bases which have either phosphonic acid and/or hydroxamic acid functionality. Since each base 311 has a different hydrogen bonding than the other three bases, these coatings can be used to sense the individual bases 311. FIG. 4 illustrates examples of the molecules for the organic coating 308 (including organic coatings 122 and 222) according to an exemplary embodiment. In FIG. 4, the example molecules of the organic coating 308 are for self-assembly on the electrodes 305 inside the nanochannel 304. FIG. 5 illustrates examples of the molecules for the organic coating 307 and 308 according to an exemplary embodiment. In FIG. 5, the example molecules of the organic coating 307 and/or 308 are for self-assembly on the electrodes 305 inside the nanochannel 304.

An example of measuring the tunneling current 318 is provided below for the left circuit while the strong transient bonds 335a and 335b (in the right circuit) hold the DNA molecule 310 in place for measurement against thermal motion (which would normally cause the DNA molecule 310 to move in the nanochannel 304). When the voltage source 318 is turned on during the bonded phase, electrical current flows through electrode 305b, through organic coating 307b, through the transient bond 315b, into base 311a (which produces the tunneling current 318), out through the transient bond 315a, out through organic coating 307a, through electrode 305a, and into the corresponding ammeter A to measure the tunneling current 318. In exemplary embodiments, numerous circuits (e.g., 2, 3, 4, 5, and/or 10) as shown in FIG. 3 can simultaneously measure the tunneling currents for numerous bases 311 of the DNA molecule 310. Each circuit would have its corresponding voltage source (like voltage source 316) and its ammeter A for measuring the tunneling current of its particular base 311 as discussed herein.

The electrodes 305a and 305b (similarly electrodes 306a and 306b) are two separate electrodes on opposite sides of the nanochannel 304 connected by a wire at the ends not in the nanochannel 304. The ends of electrodes 305a and 305b (similarly electrodes 306a and 306b) in the nanochannel 304 which have organic coating 307a and 307b (similarly organic coatings 308a and 308b) do not touch and are not connected by a wire. Instead, the transient bonds 315a and 315b (similarly transient bonds 335a and 335b) operatively connect/couple the electrodes 305a and 305b (electrodes 306a and 306b) together through the base 311a via the organic coating 307a and 307b.

The organic coating 307 on electrodes 305a and 305b is designed to form transient bonds 315a and 315b to the bases 313 of the DNA molecule 112 (and are not able to form transient bonds to the backbone 325). The transient bonds 315a and 315b formed by the organic coating 307 are weaker than the transient bond 335 formed by the organic coating 308. For example, the transient bond 335 is stronger than the transient bond 315 in the sense that the transient bond 335 is able to hold the DNA molecule 310 in place (i.e., in a fixed position) against thermal motion (thermal agitation) of the DNA molecule 310 in the nanochannel 304. The thermal motion is great enough to break the transient bonds 315 formed by the organic coating 307 on the electrodes 305a and 305b but not strong enough to break the transient bonds 335 formed by organic coating 308 on the electrodes 306a and 306b. Although the transient bond 335 is shown as being connected (bonded) to the base 311, the transient bond 335 produced by the organic coating 308 can also bond to the DNA backbone 325. Also, although not shown for conciseness, the organic coating 308 can be applied to multiple electrode pairs (e.g., 2, 3, 4, 5, etc.), and the total transient bonding strength of the multiple electrode pairs having organic coatings 308 is the sum of their respective transient bonds 335.

Further, in one implementation of an exemplary embodiment, electrodes/conductive layers 106, 206, and 306 have more contact area with their respective organic coatings 122, 222, and 308 in their respective nanopores/nanochanels 108, 208, and 304 than the electrodes/conductive layers 102, 104, 202, 204, and 305 with their respective organic coatings 109, 209, and 307.

Figure 7:
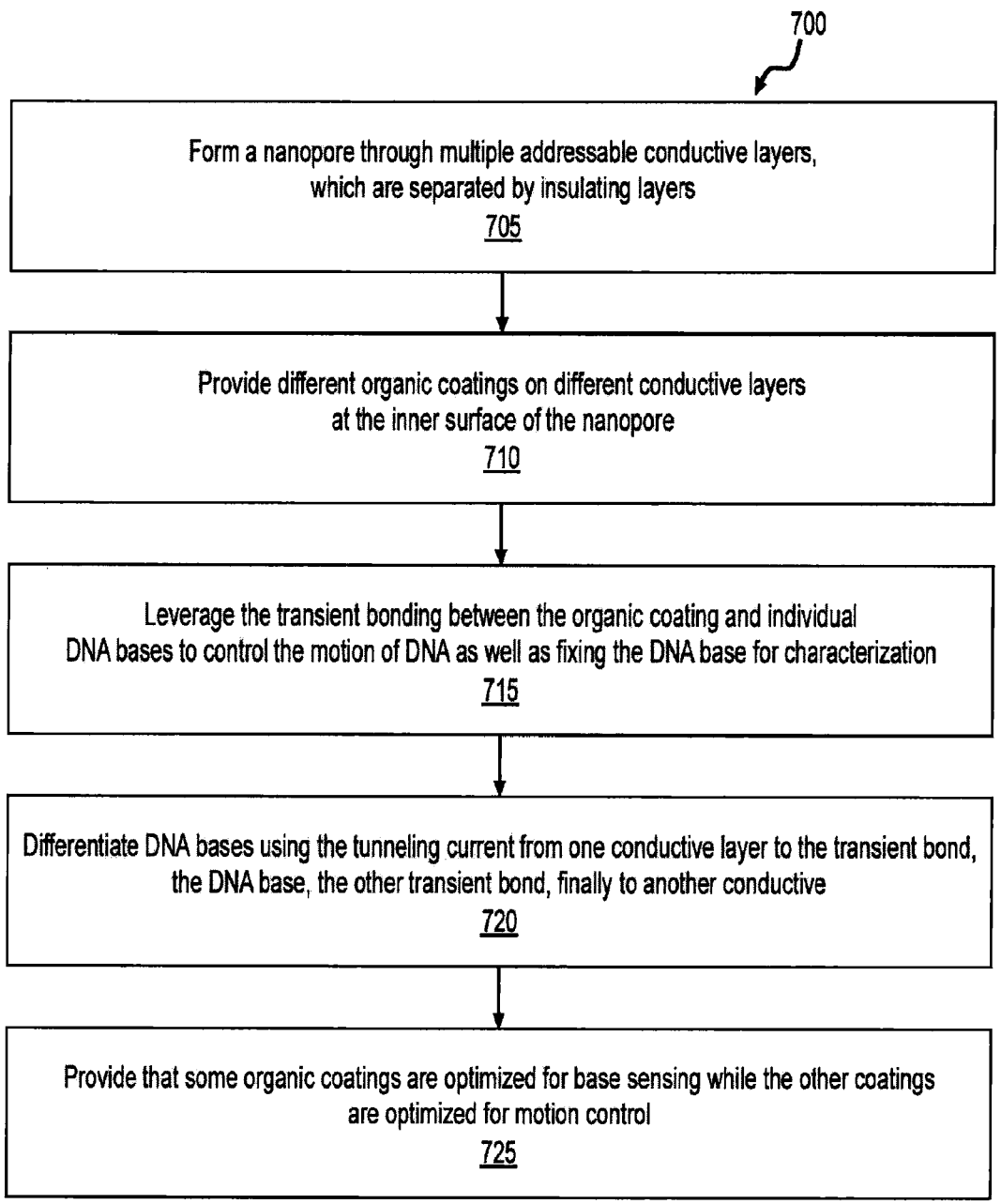
FIG. 7 illustrates a flow chart according to an exemplary embodiment.

FIG. 7 illustrates a method 700 for DNA sequencing a nanodevice according to an exemplary embodiment, and reference can be made to FIGS. 1 and 2.

At block 705, a nanopore 108, 208 is formed through multiple addressable conductive layers, which are separated by insulating layers. The addressable conductive layers 102, 104, 106, 202, 204, 206 can be addressed (i.e., have voltage individually applied as desired) by respective voltage sources 118, 119, 218, 219.

At block 710, different organic coatings (such as organic coatings 109, 122, 209, 222) are provided on different conductive layers at the inner surface of the nanopore. Some organic coatings have stronger transient bonds to bases and/or backbones of the DNA molecules 112, 212.

At block 715, the transient bonding between the organic coating and individual DNA bases and/or backbones is leveraged to control the motion of the DNA as well as to fix (hold) the DNA base for characterization. Characterization is measuring the tunneling currents 120, 121, 220, 221 as discussed herein through the conductive layers (electrodes), organic coatings, and transient bonds. Characterization (i.e., distinguishing the tunneling current signature of a base) can be performed by the computer 600.

At block 720, DNA bases are differentiated by using the tunneling current from one conductive layer to the transient bond, the DNA base, the other transient bond, and finally to another conductive layer. Differentiation of the DNA base (e.g., base 113 or 213) can be by causing the tunneling current (e.g., tunneling current 120) to be displayed (in a graph/plot of, e.g., magnitude versus time/frequency) on the display 45 of the computer 600. The computer 600 may comprise and/or be coupled to an ammeter A so that the tunneling current signature for one base 113, 213 is viewed, measured, recorded, and/or analyzed by the software application 605 (and/or a user), and the software application 605 (or user viewing the graph/plot) can differentiate one base 113, 213 from a different base 113, 213 of the DNA molecule 112, 212, based on their respective tunneling currents because the tunneling current is a signature of each particular base 113.

Also, as discussed above, a first tunneling current in base 213a can be combined with a second tunneling current in base 213b to be measured as the combined tunneling current 220 by the corresponding ammeter A. The computer 600 via software application 605 can measure, differentiate, record, display (as two graphs/plots (and/or a single graph/plot) on the display 45), and/or analyze the first and second tunneling currents forming the tunneling current 220. The computer 600 can resolve the first and second tunneling currents from the combined tunneling current 220.

At block 725, some organic coatings 109, 209 are optimized for base sensing while the other organic coatings 122, 222 are optimized for motion control (i.e., holding the DNA molecule 112, 212 in place for measurements). One conductive layer 106 coated with organic coating 109 forms a (single) stronger transient bond 123 than multiple conductive layers 102 and 104 (and more) with organic coating 209 forming multiple transient bonds 117. Likewise, a single transient bond 223 via organic coating 222 is stronger than multiple transient bonds 217 via organic coating 209.

Figure 8:
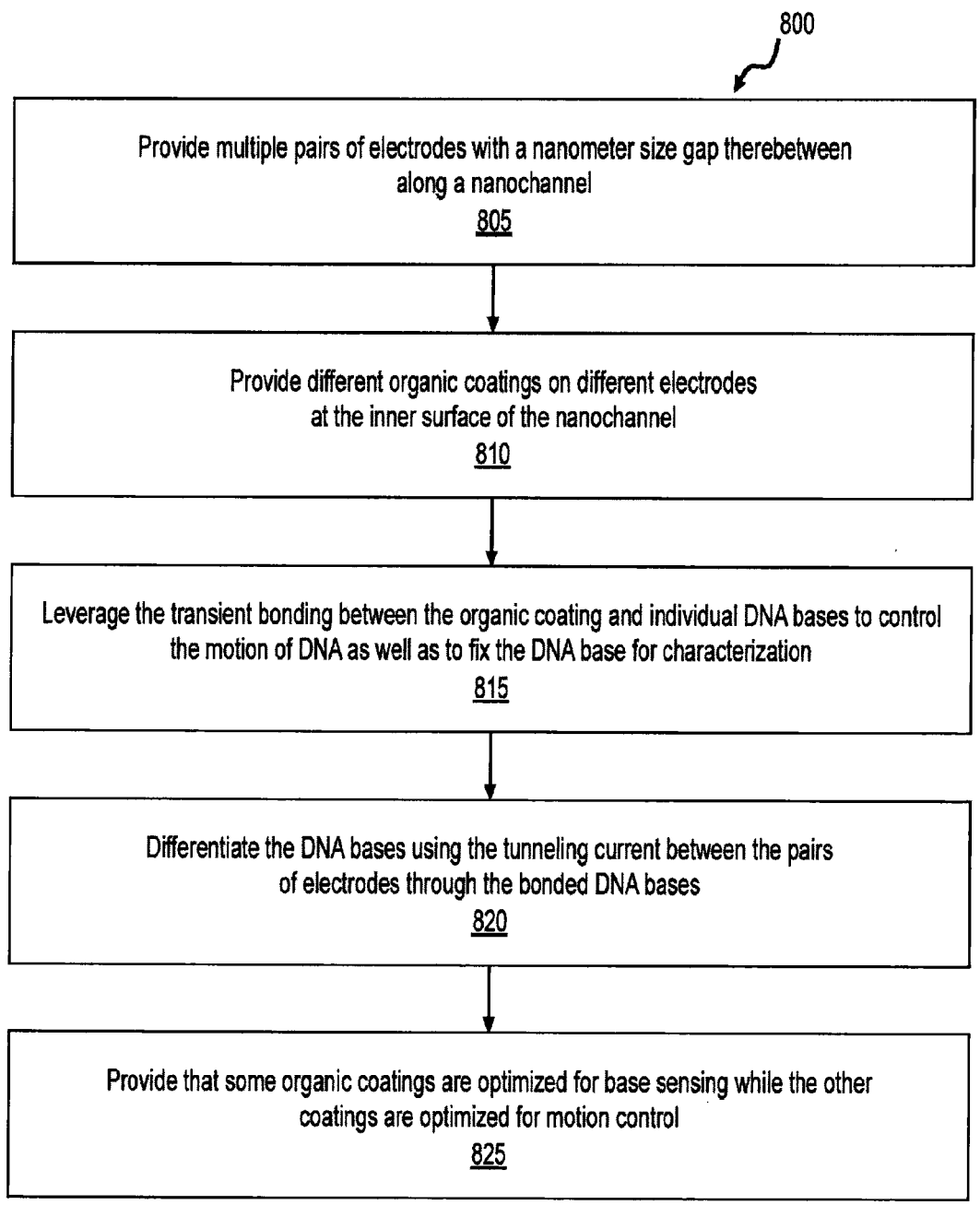
FIG. 8 illustrates a flow chart according to an exemplary embodiment.

FIG. 8 illustrates a method 800 for sequencing DNA molecules in a nanodevice according to an exemplary embodiment, and reference can be made to FIG. 3.

At block 805, multiple pairs of electrodes 305 and 306 each with a nanometer size gap there between can be formed along the nanochannel 304. Different organic coatings 307 and 308 can be applied on different electrodes 305 and 306 at the inner surface of the nanochannel 304, at block 810.

At block 815, the transient bondings 315 and 335 are formed between the organic coating 307 and 308 and individual DNA bases 311 (and/or backbone 325) to control the motion of DNA molecule 310 as well as to fix the DNA base 311 for characterization. Characterization is measuring the tunneling currents 318 and 319 as discussed herein through the electrodes, organic coatings, and transient bonds to recognize/display the individual tunneling currents (signatures) for DNA bases 311.

At block 820, each DNA base such as base 311a is differentiated using the tunneling current (e.g., tunneling current 318) between the pair of electrodes 305 through its bonded DNA base 311a. Differentiation can be performed by computer 600 (and/or a user utilizing the computer 600) as discussed herein.

At block 825, some organic coatings 307 are optimized for base 311 sensing (characterization) while the other organic coatings 308 are optimized for motion control (i.e., stopping the DNA molecule 310 against thermal motion/agitation).

Now turning to FIG. 6, FIG. 6 illustrates a block diagram of the computer 600 having various software and hardware elements for implementing exemplary embodiments.

The diagram depicts the computer 600 which may be any type of computing device and/or test equipment (including ammeters). The computer 600 may include and/or be coupled to memory 15, a communication interface 40, display 45, user interfaces 50, processors 60, and software 605. The communication interface 40 comprises hardware and software for communicating over a network and connecting (via cables, plugs, wires, electrodes, etc.) to the nanodevices discussed herein. Also, the communication interface 40 comprises hardware and software for communicating with, operatively connecting to, reading, and controlling voltage sources, ammeters, tunneling currents, etc., as discussed herein. The user interfaces 50 may include, e.g., a track ball, mouse, pointing device, keyboard, touch screen, etc, for interacting with the computer 600, such as inputting information, making selections, independently controlling different voltages sources, and/or displaying, viewing and recording tunneling current signatures for each base, etc.

The computer 600 includes memory 15 which may be a computer readable storage medium. One or more applications such as the software application 605 (e.g., a software tool) may reside on or be coupled to the memory 15, and the software application 605 comprises logic and software components to operate and function in accordance with exemplary embodiments in the form of computer executable instructions. The software application 605 may include a graphical user interface (GUI) which the user can view and interact with according to exemplary embodiments.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A nanodevice, comprising:
a substrate,
a nanochannel formed in the substrate;
a first pair of electrodes having a nanometer size gap there between;
a second pair of electrodes having a nanometer size gap there between, the first and second pair of electrodes are positioned along the nanochannel and in the substrate;
a first organic coating on an exposed surface of the first pair of electrodes at an inner surface of the nanochannel, the first organic coating forming a first transient bond between the first pair of electrodes and a base of a molecule in the nanochannel; and
a second organic coating on an exposed surface of the second pair of electrodes at the inner surface of the nanochannel, the second organic coating forming a second transient bond between the second pair of electrodes and another base of the molecule in the nanochannel;
wherein, when a first voltage is applied to the first pair of electrodes, a tunneling current is generated by the base in the nanochannel, the tunneling current traveling through the first transient bond formed to the base to be measured as a current signature for distinguishing the base; and
wherein the first organic coating comprises a functionality of resorcinol and the second organic coating comprises a functionality selected from the group consisting of phosphonic acid and hydroxamic acid.

2. The nanodevice of claim 1, wherein, when a second voltage is applied to the second pair of electrodes, another tunneling current is generated by the another base in the nanochannel, the another tunneling current traveling through the second transient bond formed to the another base to be measured as another current signature for distinguishing the another base.

3. The nanodevice of claim 2, wherein the current signature for the base and the another current signature for the another base are measured simultaneously in the nanochannel.

4. The nanodevice of claim 1, wherein the second transient bond has strength to hold the molecule in the nanochannel against thermal motion.

5. The nanodevice of claim 1, wherein a first reservoir connects to one end of the nanochannel and a second reservoir connects to another end of the nanochannel.

6. The nanodevice of claim 5, wherein a first external and a second external electrodes are in the first and second reservoirs respectively.

7. The nanodevice of claim 6, wherein the first external and second external electrodes are configured to receive an external voltage such that the first and second transient bonds are broken to move the molecule in the nanochannel.

8. The nanodevice of claim 1, wherein the substrate is a semiconductor material.

* * * * *